(12) United States Patent
Jönsson et al.

(10) Patent No.: US 8,293,683 B2
(45) Date of Patent: *Oct. 23, 2012

(54) ALKYLAMIDOPROPYL DIALKYLAMINE SURFACTANTS AS ADJUVANTS

(75) Inventors: Claes Johan Markus Jönsson, Malmö (SE); Shawn Zhu, Stormville, NY (US)

(73) Assignee: Akzo Nobel N.V., Arnhem (NL)

( * ) Notice: Subject to any disclaimer, the term of this patent is extended or adjusted under 35 U.S.C. 154(b) by 421 days.

This patent is subject to a terminal disclaimer.

(21) Appl. No.: 12/517,697

(22) PCT Filed: Dec. 3, 2007

(86) PCT No.: PCT/EP2007/063129
§ 371 (c)(1),
(2), (4) Date: Jul. 8, 2009

(87) PCT Pub. No.: WO2008/068214
PCT Pub. Date: Jun. 12, 2008

(65) Prior Publication Data
US 2010/0056375 A1  Mar. 4, 2010

Related U.S. Application Data

(60) Provisional application No. 60/873,158, filed on Dec. 6, 2006, provisional application No. 60/934,540, filed on Jun. 14, 2007.

(30) Foreign Application Priority Data

May 31, 2007 (EP) .................................. 07010792

(51) Int. Cl.
*A01N 39/02* (2006.01)
(52) U.S. Cl. ...................................................... 504/317
(58) Field of Classification Search ........................ None
See application file for complete search history.

(56) References Cited

U.S. PATENT DOCUMENTS

| 3,276,856 | A |   | 10/1966 | Esposito |         |
|-----------|---|---|---------|----------|---------|
| 5,658,855 | A |   | 8/1997  | Nalewaja et al. | |
| 5,877,112 | A |   | 3/1999  | Roberts et al. | |
| 6,130,186 | A | * | 10/2000 | Ward et al. | 504/365 |
| 6,645,914 | B1 | * | 11/2003 | Woznica et al. | 504/206 |
| 7,060,659 | B2 | * | 6/2006 | Killick et al. | 504/206 |
| 2001/0029240 | A1 |   | 10/2001 | Hasebe et al. | |
| 2002/0160916 | A1 |   | 10/2002 | Volgas et al. | |
| 2003/0153462 | A1 |   | 8/2003 | Herold et al. | |
| 2005/0215434 | A1 |   | 9/2005 | Ruiz et al. | |
| 2006/0019828 | A1 |   | 1/2006 | Becher et al. | |

FOREIGN PATENT DOCUMENTS

| AU | 2004100006 A4 | 3/2004 |
| DE | 2 327 189 | 12/1974 |
| DE | 30 02 053 A1 | 8/1980 |
| EP | 0 257 686 A1 | 3/1988 |
| EP | 0 299 654 A2 | 6/1988 |
| EP | 0 360 181 A1 | 3/1990 |
| GB | 1 339 315 | 12/1973 |
| GB | 2 233 226 A | 1/1991 |
| GB | 2 233 229 A | 1/1991 |

(Continued)

OTHER PUBLICATIONS

European Search Report for International Application No. 07010792.5; Completion Date: Oct. 9, 2007.
International Search Report for International Application No. PCT/EP2007/063129; Completion Date: Sep. 5, 2008.
De Ruiter, H.: "2, 4-D salts and adjuvants review and perspectives"; vol. 23; pp. 95-105 (2003) (XP009090474).
Derwent Abstract No. 90-092788/13 of European Publication No. 360181A, 1990.
L.L. Jansen; "Herbicidal and Surfactant Properties of Long-chain Alkylamine Salts of 2,4-D in Water and Oil Sprays," Weeds; pp. 123-130 (1965).

(Continued)

*Primary Examiner* — Alton Pryor
(74) *Attorney, Agent, or Firm* — Norris McLaughlin & Marcus, P.A.

(57) ABSTRACT

The present invention generally relates to an aqueous herbicidal formulation that comprises at least one phenoxy acid herbicide or an agriculturally acceptable salt or derivative thereof, and an alkylamidopropyl dialkylamine surfactant adjuvant, wherein said surfactant adjuvant comprises at least one surfactant having the formula (I) wherein R is a straight or branched chain, saturated or unsaturated acyl group having 6-22 carbon atoms, n is 3, and Y and Y' are, independently, an alkyl group having 1-4 carbon atoms or $(AO)_sH$, wherein AO is an alkyleneoxy group having 2-4 carbon atoms, and s is on average 1-10; provided that at least one of the groups Y and Y' is an alkyl group having 1-4 carbon atoms; or a salt thereof; or a quaternized derivative of (I) having the formula (II) wherein R is a straight or branched chain, saturated or unsaturated acyl group having from 6 to 22 carbon atoms; n is 3; Y and Y' are, independently, an alkyl group having 1-4 carbon atoms or $(AO)_sH$, wherein AO is an alkyleneoxy group having 2-4 carbon atoms, and s is on average 1-10; provided that at least one of the groups Y and Y' is an alkyl group having 1-4 carbon atoms; R2 is a C1-C4 alkyl group; and $X^-$ is an anion. The invention also relates to a method for combating unwanted vegetation which comprises applying to said unwanted vegetation an effective amount of the aforementioned herbicidal formulation.

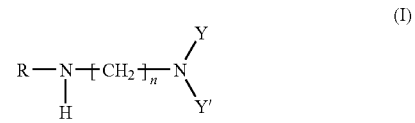

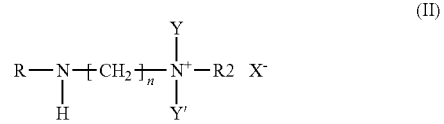

22 Claims, No Drawings

FOREIGN PATENT DOCUMENTS

| | | |
|---|---|---|
| WO | WO 81/01787 | 7/1981 |
| WO | WO 00/30452 | 6/2000 |
| WO | WO 00/64257 | 11/2000 |
| WO | WO 00/64258 | 11/2000 |
| WO | WO 01/32019 A1 | 5/2001 |
| WO | WO 01/89302 A2 | 11/2001 |
| WO | WO 01/95720 A1 | 12/2001 |
| WO | WO 02/32227 A1 | 4/2002 |
| WO | WO 02/063955 A2 | 8/2002 |
| WO | WO 02/078442 A2 | 10/2002 |
| WO | WO 02/096199 A2 | 12/2002 |
| WO | WO 02/102153 A2 | 12/2002 |
| WO | WO 03/026422 A1 | 4/2003 |
| WO | WO 2004/093546 A1 | 11/2004 |
| WO | WO 2005/087007 A1 | 9/2005 |

OTHER PUBLICATIONS

International Search Report for International Application No. PCT/US2007/008230; Completion Date: Oct. 23, 2007 (ACA6422WO).

De Ruiter, H.: "Influence of two fatty amine surfactants on Foliar Absorption, and Efficacy of 2,4-D Triethanolamine Salt,"J. Agric. Food Chem., vol. 43, pp. 3093-3097(1995).

XP-002456048; CAPLUS Abstract; Sharma et al., "Foliar penetration of picloram and 2,4-D in aspen and . . . ," J. of Plant Growth Regulations, vol. 4, No. 4, pp. 189-201 (1986).

XP-002456049; CAPLUS Abstract; Morre et al., "Mefluidide-chlorsulfuron-2,4-D surfactant combinations for roadside . . . ," Weed Science, vol. 18, No. 1, pp. 57-63 (1970).

Derwent Abstract No. 0000592267 of German Publication No. 2327189A, 1974.

Abstract of German Publication No. 3002053A1, 1980.

* cited by examiner

ALKYLAMIDOPROPYL DIALKYLAMINE SURFACTANTS AS ADJUVANTS

This case was filed under the Patent Cooperation Treaty on Dec. 3, 2007 as PCT/EP2007/063129, and claims prioity of European patent application No. 07010792.5 filed on May 31, 2006, U.S. provisional patent application No. 60/873,158 filed on Dec. 6, 2006 and U.S. provisional patent application No. 60/934,540 filed on Jun. 14, 2007.

FIELD OF THE INVENTION

The present invention relates to pesticide formulations, in particular, phenoxy acid formulations comprising alkylamidopropyl dialkylamine surfactants as adjuvants.

BACKGROUND OF THE INVENTION

Phenoxy acid herbicides are members of a family of chemicals related to the growth hormone indoleacetic acid (IAA). When sprayed on a field of crops such as wheat, rice or corn (monocots), phenoxy acid herbicides selectively induce rapid, uncontrolled growth in broad-leaf weeds (dicots) that eventually kills the unwanted vegetation and leaves the crops relatively unaffected. Phenoxy acid herbicides were independently developed in the USA and UK during World War 11 and were first introduced commercially in 1946. Today, 60 years later, the phenoxy acid herbicides still remain among the most widely used herbicides in the world.

There is a wide variety of phenoxy acid herbicides in use, further grouped into the phenoxyacetic, phenoxybutyric, and phenoxypropionic subtypes, the last itself containing the aryloxyphenoxypropionic subtype, which has the greatest number of commercial variants. 2,4-D (2,4-dichlorophenoxyacetic acid) is one well-known example, and the present invention will be exemplified using this herbicide, though the other phenoxy acids can equally well be used in the same types of formulations for the same purposes.

2,4-D acid is a white, crystalline solid, minimally soluble in water, generally formulated as soluble concentrates or emulsifiable concentrates in order to facilitate its application. The soluble concentrates are usually non-volatile, water-soluble formulations of 2,4-D amine salts such as ammonium salt, dimethylamine, isopropylamine, triethylamine, or diethanolamine salts. The emulsifiable concentrates are formulations of, for example, 2,4-D esters with high volatility, such as ethyl, propyl, isopropyl, butyl, isobutyl, or amyl esters, or 2,4-D esters with low volatility, such as butoxyethyl or 2-ethylhexyl esters.

The terms "ammonium" and "monoammonium" are used herein to refer to inorganic ammonium salts, i.e., $NH_4^+$, unless the context demands otherwise. Phenoxy acid rates and concentrations given herein, even where the phenoxy acid is present as a salt or salts, are expressed as acid equivalent (ae)—by acid equivalent is meant that portion of a formulation that, theoretically, could be converted back to the parent acid and represents the original acid portion of the molecule—unless the context demands otherwise.

It has been generally accepted that, with the same 2,4-D acid equivalent, the 2,4-D esters are more effective than the 2,4-D amine salts, although their herbicidal effect is slower. The highly volatile esters are also more effective than esters with low volatility, but can cause undesired damage to the surrounding environment because of their volatility. The risk of unwanted damage caused by volatilisation has caused the application of highly volatile ester formulations to be regulated and restricted.

A commonly practised way to enhance the performance of pesticide products is to add an adjuvant either to the pesticide formulation or to the spray tank just before application. An adjuvant can maximise the activity of the pesticide product by a variety of functions, such as increasing spray droplet retention on difficult to wet leaf surfaces, or facilitate penetration of the pesticide into the plant cuticle.

Substances traditionally utilised as adjuvants are, for example, petroleum or natural based oils, inorganic salts, polymers, polyols, and surfactants. Surfactants have proved to be very useful and versatile adjuvants for many applications, but selecting the optimum surfactant system and the optimum concentration for a specific pesticide application is often a challenge.

A type of surfactant that has proved to be especially useful as a pesticide adjuvant in several applications is the amine derivative. An amine surfactant with a primary, secondary or tertiary amine function can react with an acid to form a salt. By using an amine surfactant to neutralise all, or a part of, the 2,4-D acid, it is possible to create a highly concentrated, water-soluble 2,4-D formulation with a built-in adjuvant system.

U.S. Pat. No. 3,276,856 discloses compositions containing dimethyl-($C_{12}$-$C_{18}$ alkyl)amine salts of phenoxy acid herbicides, e.g. 2,4-dichlorophenoxyacetic acid. These compositions have a high level of active herbicidal ingredient and improved emulsification properties, and are used to make water-in-oil emulsions.

US 2005/0215434 teaches to use herbicidal 2,4-D-amine salts, e.g. dimethylamine or diethanolamine salts, in combination with a humectant, such as ethoxylated fatty amines or amine oxides, an anti-freeze, and an anti-foaming agent in order to make liquid compositions that are non-volatile, soluble in water, and stable at low temperatures.

WO 02/32227 describes how to make a non-aqueous homogeneous liquid herbicide composition comprising a lipophilic carrier. Such non-aqueous compositions are not in accordance with the present invention.

WO 01/32019 discloses emulsions comprising a) pesticides and b) fatty acid amidoamines and/or their quaternized derivatives. However, the products disclosed therein are made by, in a first step, reacting fatty acids and unsubstituted ethylene amines. The use of unsubstituted amines will inevitably result in the formation of by-products during the manufacturing, such as hydrophobic diamides, leading to various problems and reduced efficacy. The production of an alkylene oxide-substituted amine B, as disclosed in the examples, by alkoxylation of the unsubstituted amide obtained in the first step, is thus an overall costly multi-step process and will result in the formation of a number of by-products. Hence, alternative, more cost-efficient products are desired. Further, the ethyleneamine-based amides have an inferior biodegradability compared to the propylenediamine-based amides.

In EP 1 289 362 compositions are disclosed containing a) a pesticide and b) an adjuvant which could be an amidoamine. An amidoamine used in the working examples is a cocoamide of N,N-bishydroxyethyl-1,3-propylenediamine, which is used together with the pesticides glyphosate and azoxystrobin respectively. However, the production of this bishydroxyethyl substituted amidoamine is costly, results in the formation of a number of by-products, and the bishydroxyethyl substituted amidoamines have too low efficacy. Hence, more cost-efficient products are desired.

In an article by L. L. Jansen in *Weeds* (1965), 13(2), 123-130, various amine salts of 2,4-dichlorophenoxyacetic acid are disclosed and their herbicidal activity investigated by greenhouse evaluation. Fatty amines, such as coco, soya, oleyl, and tallow alkylamine, were used as such or as ethoxylated or propoxylated derivatives. Further amine derivatives used were di(long chain alkyl) amines, such as di-coco and di-(H-tallow alkyl)amine, tertiary amines such as methyl-di-(coco alkyl)amine and dimethyl-(coco alkyl)amine, and N-alkyl-1,3-propane-diamines, such as N-oleyl-1,3-propanediamine and N—($C_{1-9}$ alkyl)-N,N'-diethyl-1,3-propanediamine. The salts were used in water and/or oil.

As disclosed by Jansen, alkylamine based adjuvants have been used in the past and have proven to have bioefficacy-enhancing ability to 2,4-D. The choice of surfactant can be important, since there are wide variations among surfactants in terms of their ability to enhance the herbicidal efficacy of phenoxy acids for particular applications. Dimethyl cocoalkyl amine of the formula

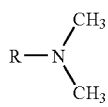

where R=coco alkyl, was considered to be most closely related to the structure of the adjuvants of the present invention, and was thus chosen as one of the references in the Examples of the present invention.

However, there is still a need for finding a suitable adjuvant with good environmental properties in addition to a good efficacy enhancing property, and it is desirable to develop a stable aqueous phenoxy acid salt formulation which (i) has high phenoxy acid ae loading, (ii) is stable and provides better efficacy than that of commercial phenoxy acid salt formulations, and (iii) has an overall better biodegradability.

These and other objectives are met by the adjuvants and herbicidal formulations of the present invention.

SUMMARY OF THE INVENTION

The present invention relates to phenoxy acid formulations having good bioefficacy and comprising as an adjuvant at least one alkylamidopropyl dialkylamine surfactant with good biodegradation. As used in this application, the term alkylamidopropyl dialkylamine means an alkylamidopropylamine having an amido function and a tertiary basic nitrogen atom. The groups attached to the tertiary basic nitrogen atom are lower alkyl groups. By lower alkyl is here meant an alkyl group or hydroxy-substituted alkyl group having 1-4 carbon atoms. The invention also pertains to formulations comprising phenoxy acid salts or other derivatives of these acids. Also the use of quaternised derivatives of the alkylamidopropyl dialkylamine is claimed, though for toxicity reasons the quaternised derivatives are less preferred.

DETAILED DESCRIPTION OF THE INVENTION

The present invention relates to pesticide formulations, in particular, to phenoxy acid formulations comprising alkylamidopropyl dialkylamine surfactants as adjuvants. More particularly, the present inventors have discovered that certain alkylamidopropyl dialkylamines not only provide enhanced bioefficacy to phenoxy acid formulations, but also a favourable biodegradability profile. The present invention also makes it possible to develop a stable aqueous ammonium, alkylammonium, potassium, or mixed salts phenoxy acid composition, preferably an ammonium or alkylammonium phenoxy acid composition, having high ae loading and which is stable, provides better efficacy than that of commercial standard phenoxy salt formulations, comprises less by-products, is more cost-efficient, and has good biodegradation.

The class of alkylamidopropyl dialkylamine surfactants useful in the context of the present invention is represented by the following formula:

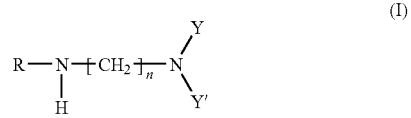

wherein R is a straight or branched chain, saturated or unsaturated acyl group having 6-22, preferably 6-18, more preferably 6-14, even more preferably 6-10, and most preferably 8-10 carbon atoms, n is 3, and Y and Y' are, independently, an alkyl group having 1-4 carbon atoms, preferably 1-2 carbon atoms, and most preferably 1 carbon atom, or $(AO)_sH$, wherein AO is an alkyleneoxy group having 2-4 carbon atoms, preferably 2 carbon atoms, and s is on average 1-10, preferably 1-4, and most preferably 1-2; provided that at least one, preferably both, of the groups Y and Y' is an alkyl group having 1-4 carbon atoms; or a salt thereof.

In one embodiment, R is a straight or branched chain, saturated or unsaturated acyl group having from 6 to 18 carbon atoms; Y and Y' are a $C_1$-$C_2$ alkyl group; and n is 3.

In another embodiment, R is a straight or branched chain, saturated or unsaturated acyl group having from 6 to 14 carbon atoms; Y and Y' are a methyl group; and n is 3.

In one further embodiment R is a straight or branched chain, saturated or unsaturated acyl group having from 6 to 10 carbon atoms, Y and Y' are a methyl group; and n is 3.

In still another embodiment, the alkylamidopropyl dialkylamine has been quaternised and has the formula

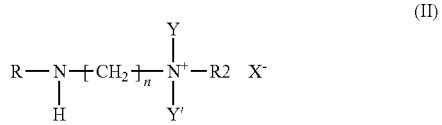

wherein R is a straight or branched chain, saturated or unsaturated acyl group having from 6 to 22, preferably 6-18, more preferably 6-14, and most preferably 6-10 carbon atoms; n is 3; Y and Y' are, independently, an alkyl group having 1-4 carbon atoms or $(AO)_sH$, wherein AO is an alkyleneoxy group having 2-4 carbon atoms, preferably 2 carbon atoms, and s is on average 1-10, preferably 1-4, and most preferably 1-2; provided that at least one, preferably both, of the groups Y and Y' is an alkyl group having 1-4 carbon atoms; R2 is a $C_1$-$C_4$ alkyl group; and $X^-$ is a conventional anion, such as $Cl^-$, $Br^-$, $I^-$, $H_2PO_4^-$, $HSO_4^-$, $H_3C$—$OSO_3^-$, $HCO_3^-$ and $H_3C$—$OCO_2^-$. Further anions can be present after an exchange with one or more of the anions mentioned, particularly an exchange with the $HCO_3^-$ and $H_3C$—$OCO_2^-$ anions. For example, the latter anions may also be exchanged to carboxylate anions derived from acids such as acetic acid, propionic acid, 2-ethylhexanoic acid, fatty acids, such as coco fatty acid and tallow fatty acid, salicylic acid, lactic acid, gluconic acid, citric acid, benzoic acid and ethylenediaminetetraacetic acid; and to anions derived from other types of acids, such as methanesulfonic acid, p-toluenesulfonic acid, boric acid and acid clay.

The most preferred derivatives are the ones where Y and Y' are lower alkyl groups.

The invention thus pertains to an aqueous, preferably homogeneous, composition comprising at least one phenoxy acid herbicide or an agriculturally acceptable salt or derivative thereof, and a surfactant adjuvant according to formula (I) or (II) above, or a salt thereof.

However, the quaternised derivatives are less preferred because of their higher toxicity. Further, when using the compounds according to formula (I) as adjuvants, it is possible to obtain more concentrated formulations than obtainable when products of formula II are used.

Specific examples of alkylamidopropyl dialkylamine surfactants useful in the context of the present invention include, but are not limited to, N-[3-(dimethylamino)propyl] ($C_8$-$C_{10}$) amide, N-[3-(dimethylamino)propyl]cocoamide, and N-[3-(dimethylamino)propyl] (rape-seed) amide.

The phenoxy acid herbicide preferably is a phenoxyacetic acid herbicide, phenoxybutyric acid herbicide, phenoxypropionic acid herbicide, aryloxy-phenoxypropionic acid herbicide, or a mixture thereof. The most preferred phenoxy acid herbicides are 4-chlorophenoxyacetic acid (4-CPA), (2,4-dichlorophenoxy)acetic acid (2,4-D), (3,4-dichlorophenoxy)acetic acid (3,4-DA), 4-chloro-o-tolyloxyacetic acid (MCPA), S-ethyl 4-chloro-o-tolyloxythioacetate (MCPA-thioethyl), 4-(4-chlorophenoxy)butyric acid (4-CPB), 4-(2,4-dichlorophenoxy)butyric acid (2,4-DB), 4-(3,4-dichlorophenoxy)butyric acid (3,4-DB), 4-(4-chloro-o-tolyloxy)butyric acid (MCPB), (RS)-2-(3-chlorophenoxy)propionic acid (cloprop), (RS)-2-(4-chlorophenoxy)propionic acid (4-CPP), (RS)-2-(2,4-dichlorophenoxy)propionic acid (dichlorprop), (R)-2-(2,4-dichlorophenoxy)propionic acid (dichlorprop-P), (RS)-2-(3,4-dichlorophenoxy)propionic acid (3,4-DP), (RS)-2-(2,4,5-trichlorophenoxy)propionic acid (fenoprop), (RS)-2-(4-chloro-o-tolyloxy)propionic acid (mecoprop), (R)-2-(4-chloro-o-tolyloxy)propionic acid (mecoprop-P), (RS)-2-[4-(3,5-dichloro-2-pyridyloxy)phenoxy]propionic acid (chlorazifop), (R)-2-[4-(5-chloro-3-fluoro-2-pyridyloxy)phenoxy]propionic acid (clodinafop), (RS)-2-[4-(4-chlorophenoxy)phenoxy]propionic acid (clofop), (R)-2-[4-(4-cyano-2-fluorophenoxy)phenoxy]propionic acid (cyhalofop), (RS)-2-[4-(2,4-dichlorophenoxy)phenoxy]propionic acid (diclofop), (RS)-2-[4-(6-chloro-1,3-benzoxazol-2-yloxy)phenoxy]propionic acid (fenoxaprop), (R)-2-[4-(6-chloro-1,3-benzoxazol-2-yloxy)phenoxy]propionic acid (fenoxaprop-P), (RS)-2-[4-(6-chloro-1,3-benzothiazol-2-yloxy)phenoxy]propionic acid (fenthiaprop), (RS)-2-{4-[5-(trifluoromethyl)-2-pyridyloxy]phenoxy}propionic acid (fluazifop), (R)-2-{4-[5-(trifluoromethyl)-2-pyridyloxy]phenoxy}propionic acid (fluazifop-P), (RS)-2-{4-[3-chloro-5-(trifluoromethyl)-2-pyridyloxy]phenoxy}propionic acid (haloxyfop), (R)-2-{4-[3-chloro-5-(trifluoromethyl)-2-pyridyloxy]phenoxy}propionic acid (haloxyfop-P), (RS)-2-[2-[4-(3,5-dichloro-2-pyridyloxy)phenoxy]propionyl]-isoxazolidine (isoxapyrifop), (R)-2-[4-(6-chloro-1,3-benzoxazol-2-yloxy)-phenoxy]-2'-fluoro-N-methylpropionanilide (metamifop), 2-isopropylidene-aminooxyethyl (R)-2-[4-(6-chloroquinoxalin-2-yloxy)phenoxy]propionate (propaquizafop), (RS)-2-[4-(6-chloroquinoxalin-2-yloxy)phenoxy]propionic acid (quizalofop), (R)-2-[4-(6-chloroquinoxalin-2-yloxy)phenoxy]propionic acid (quizalofop-P), (RS)-2-[4-(α,α,α-trifluoro-p-tolyloxy)phenoxy]propionic acid (trifop), (2,4,5-trichlorophenoxy)acetic acid (2,4,5-T), 4-(2,4,5-trichlorophenoxy)butyric acid (2,4,5-TB), and mixtures thereof.

In addition to the surfactant adjuvants mentioned here, the herbicidal formulations of the present invention can contain additional components including, but not limited to, additional surfactants or other additives. It is preferred that when the formulations of the invention do contain such additional components, such additional components are substantially non-irritating to the eye, substantially non-toxic to aquatic life, and have acceptable bio-efficacy. Such additional components include surfactants such as cationic, anionic, non-ionic, and amphoteric surfactants. Examples of these surfactants are disclosed in McCutcheon's *Emulsifiers and Detergents*, North America Edition, 2000. Non-limiting examples of preferred cationic surfactants are alkoxylated alkylamine and its quaternary derivative, alkoxylated etheramine and its quaternary derivative, alkyl amine oxide, alkyl amidopropyl amine oxide, and alkyl trimethyl ammonium chloride. Non-limiting examples of preferred anionic surfactants are alkylsulfate, alkylethersulfate, alkylsulfonate, alkylsulfosuccinate, alkoxylated phosphate ester, alkyl α-olefin sulfonate, alkyl n-methyl taurate, fatty acid isethionate, and alkyl ether carboxylate. Non-limiting examples of preferred nonionic surfactants are sorbitan ester and its alkoxylated derivative, sorbitol ester and its alkoxylated derivative, fatty acid ester, castor oil alkoxylate, alcohol alkoxylate, alkanolamide, alkanolamide alkoxylate, and alkylpolyglycoside. Non-limiting examples of preferred amphoteric surfactants are alkylbetaine, alkylamidopropyl betaine, alkylamphoacetate, alkylamphodiacetate, alkylamphocarboxylate, alkylamphopropionate, alkylamphodipropionate, alkylamidoamine carboxylate, alkylamphohydroxypropyl sulfonate, alkylsultaine, alkylamidopropyl hydroxyl sultaine, alkyl dihydroxyethyl glycinate, alkylaminopropionate, and blends thereof.

An aqueous composition is herein defined to be a composition wherein water is present in an amount such that it is the sole or predominant solvent. If more than one solvent is present, then the sum of the water and water-miscible solvents (at 20° C.) should be greater than the amount of lipophilic, non-water-miscible solvents, which includes oils that are used as lipohilic carrier and/or adjuvant. In such mixtures of solvents it is preferred that at least 10, preferably 20, more preferably 35, and most preferably at least 50% by weight of the total weight of water and water-miscible solvents (at 20° C.) is water. Preferably water is the sole solvent, which includes compositions wherein traces of other solvents are present, since for environmental reasons the use of hydrophobic solvents is not desirable. Traces are herein defined as being an amount of up to 2, preferably up to 1% by weight, based on the total weight of all solvent.

In absolute terms, the compositions may comprise from 0.1 up to 99.99% by weight of water. The lower limit of 0.1% water is only used when an almost pure mixture of herbicide and surfactant according to the invention is combined with just a little water. Such highly concentrated mixtures have the advantage that they can be transported at low cost. However, since producing such highly concentrated compositions requires stringent conditions, it is preferred that aqueous compositions be used that comprise from about 10 to about 99.99% by weight of solvents, based on the weight of the total composition. The highly diluted compositions, comprising solvents in an amount of about 90 to about 99.99% by weight, based on the weight of the total composition, are typically used when applying the herbicide to plants after dilution of a more concentrated composition according to the invention.

The pH of the aqueous formulations may vary and is suitably in the range of 2-11, preferably 3-9, and most preferably 4-8. If only a part of the acid is neutralised by the amine surfactant, an additional alkaline compound, e.g. a smaller amine, ammonia or KOH, may be used to modify the pH to the desired value. Preferred pH-modifiers are short-chain amine compounds, such as dimethylamine, isopropylamine, triethylamine or diethanolamine.

An advantage of formulating 2,4-D acid together with both an amine surfactant and a small amine, for example dimethylamine, is that it is possible to obtain very concentrated formulations without formulation instability and with a balanced amount of amine surfactant adjuvant. All the adjuvant-containing formulations in the example below have the same concentration of 2,4-D acid (600 g ae/liter) as the commercially available 2,4-D dimethylamine salt where no surfactant adjuvant is present in the formulation. Another advantage of formulating 2,4-D acid and water with the amine surfactants according to formula (I), or with a mixture of surfactants of formula (I), small amines, and other additives, is the ease of preparation. The components form a non-viscous, clear formulation regardless of the addition order, just by stirring at room temperature. If desired, heating may be used to speed up the homogenisation process. A convenient procedure for making a phenoxy acid salt solution is as follows. Phenoxy acid, surfactant adjuvant, dimethylamine or any other amine of low molecular weight, and water are added to a blending vessel and stirred at room temperature or with slight heating (up to 60° C.) until homogeneous. An additional amount of the amine of low molecular weight is added to adjust the pH of the formulation (measured on a 1% solution of the formulation in water) to 4.5-5.5, rendering the formulation water-soluble.

The compositions according to the invention may be concentrates, or diluted, "ready to use", solutions.

The concentrations of the components may vary within wide limits, and a herbicide formulation may contain 0.01-99.9% by weight of a phenoxy acid herbicide and an amount of 0.01-70% by weight of an adjuvant compound of formula (I) according to the invention.

As a water solution concentrate, the concentrations are normally in the range of 4-70%, preferably 20-40%, for the herbicide and 2-50%, preferably 2-20%, for the adjuvants, whereas for the ready-to-use solutions the corresponding ranges are 0.01-4% and 0.01-4%; for all compositions the remainder being water and optional additional components.

The adjuvant and the optional additional components may either be mixed in the concentrate or be tank-mixed just before spraying the solution.

The concentrated herbicidal compositions according to the present invention preferably contain
  a) 100-800 g ae/liter of phenoxy acid herbicide
  b) 25-400 g/liter of adjuvant having the formula (I).

In another embodiment the weight ratio of phenoxy acid to the alkylamidopropyl dialkylamine surfactant of the invention is between 1:2 and 25:1 (i.e. the ratio between the weight of the ae of the herbicide and the weight of the amine surfactant). Typically, the weight ratio of phenoxy acid ae to the alkylamidopropyl dialkylamine surfactant of the invention is between 2.5:1 and 20:1, in yet another embodiment of the invention it is between 3:1 and 15:1.

A herbicidal composition according to the invention may comprise other optional components such as ammonium sulfate, potassium sulfate, potassium chloride, sodium sulfate, urea, glycerol, glycols, polyglycols, or mixtures thereof. A contemplated composition may optionally include a synergist, quick-burn additive, humectant, co-herbicide, other pesticides, other amine compounds, e.g. dimethylamine, isopropylamine, triethylamine, or diethanolamine, dye, pigment, corrosion inhibitor, thickener, dispersing agent, sequestrant, defoamer, antifreeze, pour-point depressant, anti-gelling agents, pH-modifiers, preservatives, hydrotropes, solvents, process aids, or mixtures thereof. Combinations of phenoxy acid salts and co-herbicide salts are specifically contemplated by the present invention. Preferably, additives used in phenoxy acid compositions of the present invention possess sufficient solubility or dispersibility in a concentrated aqueous phenoxy acid solution at a pH of from about 4 to about 7 to allow desired concentrations to be attained.

Compositions of the present invention generally can be prepared by mixing the phenoxy acid salt solution, prepared as outlined above, together with other ingredients in a suitable mixing vessel with agitation, such as a blender.

This invention also relates to a herbicidal method of using a composition according to the invention in an amount effective to kill or control unwanted vegetation by applying an optionally diluted composition to foliage of the vegetation to be killed or controlled.

The phenoxy acid formulation of the invention should be applied to plant foliage at an application rate sufficient to give the desired effect. Application rates are usually expressed as amount of phenoxy acid (g ae) per unit area of land treated, e.g. grams ae per hectare (g ae/ha). What constitutes a "desired effect" varies according to the standards and practice of those who investigate, develop, market, and use phenoxy acid products. For example, the amount of phenoxy acid ae applied per unit area to give, consistently and reliably, at least 85% control of a plant species as measured by growth reduction or mortality is often used to define a commercially effective rate.

Preferred compositions of the invention provide enhanced herbicidal efficacy by comparison with commercial standard formulations of phenoxy acids. "Herbicidal efficacy" as used herein refers to any observable measure of control of plant growth, which can include one or more of the actions of (1) killing, (2) inhibiting growth, reproduction or proliferation, and (3) removing, destroying, or otherwise diminishing the occurrence and activity of plants.

The selection of biologically effective application rates for a specific phenoxy acid composition, such as a composition of the present invention, is within the skill of the ordinary agricultural scientist. Those of skill in the art will likewise recognise that individual plant conditions, weather, and growing conditions, as well as the specific formulation selected, will influence the degree of biological effectiveness achieved in practising this invention. Useful application rates can therefore depend upon all of the above conditions. Much information is known about appropriate application rates for phenoxy acid formulations in general. Various application methods can be employed, including broadcast spraying, directed spraying or wiping the foliage with a diluted composition of this invention. Depending on the degree of control desired, the age and species of the plants, weather conditions, and other factors, typically the phenoxy acid application rate is a herbicidally effective amount of about 0.1 to about 10 kg ae/ha and preferably from about 0.25 to about 2.5 kg ae/ha, although greater or lesser amounts may be applied.

The present invention will now be illustrated by the following nonlimiting examples.

General Experimental

Formulations were made up according to the scheme presented in Table 1. 2,4-D acid, surfactant adjuvant, dimethylamine (ex Fluka), and water were added to a blending vessel and stirred at room temperature or with slight heating (up to 60° C.) until homogeneous. The amount of surfactant was the same in all formulations, whereas the addition of dimethylamine varied between the formulations. Dimethylamine was added to adjust the pH of the formulation (measured on a 1% solution of the formulation in water) to 4.5-5.5, rendering the formulation water-soluble. After preparation the formulations were sent for greenhouse testing.

TABLE 1

| Formulation | Surfactant | Amount of surfactant (g/l) | Amount of 2,4-D acid (g/l) | Amount of dimethylamine (30%) (g/l) | Amount of water |
|---|---|---|---|---|---|
| 1 | N-[3-(dimethylamino)propyl] ($C_8$-$C_{10}$) amide | 204 | 600 | 202.8 | Balance up to 1 liter |
| 2 | N-[3-(dimethylamino)propyl] cocoamide | 204 | 600 | 216.6 | Balance up to 1 liter |
| Examples of prior art: | | | | | |
| A (comparison) | Cocodimethylamine, Armeen ® 2MCD | 204 | 600 | 182.4 | Balance up to 1 liter |
| B (comparison) | Cocoamide of N,N-bishydroxyethyl-1,3-propylenediamine | 204 | 600 | 224.4 | Balance up to 1 liter |

Note:
The pH of the formulations (1% in water) was adjusted to 4.5-5.5 using dimethylamine.

Example 1

The alkylamidopropyl dialkylamines of the invention demonstrate good bioefficacy compared to the prior art products. In the provided examples the herbicidal efficacy of 2,4-D formulations on *Brassica Napus* is presented. In Tables 2-3, a formulation containing an adjuvant according to the invention (formulation 1; see Table 1) is compared to a formulation containing a cocodimethylamine (formulation A; see Table 1), and in Tables 4 and 5 formulation 1 is compared to a formulation containing the cocoamide of N,N-bishydroxyethyl-1,3-propylenediamine (formulation B see Table 1)

Formulations were made up according to the scheme presented in Table 1 by the procedure described in General Experimental.

Three different doses of the formulations were applied to different sets of plants containing 100, 200, and 400 g of 2,4-D acid per hectare, respectively. The formulations were diluted in tap water and applied as 200 liters of diluted spray solution per hectare. The aqueous herbicide formulations were sprayed on the plants by using a laboratory track sprayer fitted with a Lurmark "DIF 80" nozzle, set up to deliver 200±20 L/ha using gear 4 with a pressure of 210 Pa (30 psi). A calibration run was made with two Petri dishes containing paraffin oil at 1 m apart. The mean value obtained was 196 L/ha.

The results 21 days and 30 days after treatment compared to compound A are collected in Tables 2-3 respectively. The results 10 days and 21 days after treatment compared to compound B are collected in Tables 4 and 5 respectively. The results are weighted averages of three replicates.

The experiments were assessed according to the amount of green life growth and regrowth 10, 21 days and 30 days after spraying for *Brassica napus*. A score of 0-100% was used, where 100% is a totally dead plant (100 percent control), and for example a 50% reduction in the amount of green growth present was scored by a comparison to the best untreated plant, the latter scoring 0% (0 percent control).

TABLE 2

The herbicidal activity (percent control) on *Brassica Napus* (rape-seed), 21 days after treatment

| Herbicide dose (g a.e. $ha^{-1}$) | 100 | ±S.E.* | 200 | ±S.E.* | 400 | ±S.E.* |
|---|---|---|---|---|---|---|
| Formulation 1 | 55 | 2.9 | 68.3 | 8.8 | 83.3 | 6 |
| Formulation A (comparison) | 45 | 2.9 | 55 | 0 | 73.3 | 8.3 |

*S.E. = standard error
100 g a.e. $ha^{-1}$ = 34 g $ha^{-1}$ of surfactant = 0.02% (w/w) in 200 liters of spray solution
200 g a.e. $ha^{-1}$ = 68 g $ha^{-1}$ of surfactant = 0.03% (w/w) in 200 liters of spray solution
400 g a.e. $ha^{-1}$ = 136 g $ha^{-1}$ of surfactant = 0.07% (w/w) in 200 liters of spray solution

TABLE 3

The herbicidal activity (percent control) on *Brassica Napus* (rape-seed), 30 days after treatment

| Herbicide dose (g a.e. $ha^{-1}$) | 100 | ±S.E.* | 200 | ±S.E.* | 400 | ±S.E.* |
|---|---|---|---|---|---|---|
| Formulation 1 | 63.3 | 1.7 | 85 | 7.6 | 93.3 | 6.7 |
| Formulation A (comparison) | 60 | 0 | 71.7 | 1.7 | 88.3 | 7.3 |

*S.E. = standard error
100 g a.e. $ha^{-1}$ = 34 g $ha^{-1}$ of surfactant = 0.02% (w/w) in 200 liters of spray solution
200 g a.e. $ha^{-1}$ = 68 g $ha^{-1}$ of surfactant = 0.03% (w/w) in 200 liters of spray solution
400 g a.e. $ha^{-1}$ = 136 g $ha^{-1}$ of surfactant = 0.07% (w/w) in 200 liters of spray solution In the overall comparison of the formulations for the different doses it was found that formulation 1 perform better than the prior art formulation A.

It is shown in this example that the efficacy of 2,4-D on *Brassica Napus* can be enhanced using surfactant adjuvants already at very low concentrations of surfactant. When 2,4-D is applied at 200 g per hectare, the surfactant concentration in the spray tank is only 0.03% (w/w), which is about one third of the generally recommended adjuvant dose in herbicidal formulations, and formulation 1 performs better than any of the other tested formulations 30 days after treatment using this dose.

TABLE 4

The herbicidal activity (percent control) on *Brassica Napus* (rape-seed), 10 days after treatment

| Herbicide dose (g a.e. ha$^{-1}$) | 100 | ±S.E.* | 200 | ±S.E.* |
|---|---|---|---|---|
| Formulation 1 | 31.6 | 1.7 | 45.0 | 2.9 |
| Formulation B (comparison) | 26.7 | 1.7 | 33.3 | 1.7 |

*S.E. = standard error
100 g a.e. ha$^{-1}$ = 34 g ha$^{-1}$ of surfactant = 0.02% (w/w) in 200 liters of spray solution
200 g a.e. ha$^{-1}$ = 68 g ha$^{-1}$ of surfactant = 0.03% (w/w) in 200 liters of spray solution

TABLE 5

The herbicidal activity (percent control) on *Brassica Napus* (rape-seed), 21 days after treatment

| Herbicide dose (g a.e. ha$^{-1}$) | 100 | ±S.E.* | 200 | ±S.E.* |
|---|---|---|---|---|
| Formulation 1 | 55 | 2.9 | 68.3 | 8.8 |
| Formulation B (comparison) | 51.7 | 1.7 | 55 | 2.9 |

*S.E. = standard error
100 g a.e. ha$^{-1}$ = 34 g ha$^{-1}$ of surfactant = 0.02% (w/w) in 200 liters of spray solution
200 g a.e. ha$^{-1}$ = 68 g ha$^{-1}$ of surfactant = 0.03% (w/w) in 200 liters of spray solution In the overall comparison of the formulations for the different doses it was found that formulation 1 perform better than the prior art formulation B.

Example 2

In the provided example the herbicidal efficacy of 2,4-D formulations on *Stellaria media* (common chickweed) is presented.

Formulations were made up according to the scheme presented in Table 1 by the procedure described in General Experimental.

Three different doses of the formulations were applied to different sets of plants containing 750, 1500 and 2000 g of 2,4-D acid per hectare, respectively. The formulations were diluted in tap water and applied as 200 liters of diluted spray solution per hectare. The aqueous herbicide formulations were sprayed on the plants by using a laboratory track sprayer fitted with a Lurmark "DIF 80" nozzle, set up to deliver 200±20 L/ha using gear 4 with a pressure of 210 Pa (30 psi). A calibration run was made with two Petri dishes containing paraffin oil at 1 m apart. The mean value obtained was 196 L/ha.

The results 10 days, 21 days and 30 days after treatment compared to compound B are collected in Tables 6-8 respectively.

The results are weighted averages of three replicates.

The experiments were assessed according to the amount of green life growth and regrowth 10, 21 days and 30 days after spraying for *Stellaria media*. A score of 0-100% was used, where 100% is a totally dead plant (100 percent control), and for example a 50% reduction in the amount of green growth present was scored by a comparison to the best untreated plant, the latter scoring 0% (0 percent control).

TABLE 6

The herbicidal activity (percent control) on *Stellaria media*, 10 days after treatment

| Herbicide dose (g a.e. ha$^{-1}$) | 750 | ±S.E. | 1500 | ±S.E. |
|---|---|---|---|---|
| Formulation 1 | 28.3 | 1.7 | 60.0 | 7.6 |
| Formulation 2 | 25.0 | 2.9 | 53.3 | 1.7 |
| Formulation B (comparison) | 23.3 | 1.7 | 48.3 | .4 |

*S.E. = standard error
750 g a.e. ha$^{-1}$ = 253 g ha$^{-1}$ of surfactant = 0.13% (w/w) in 200 liters of spray solution
1500 g a.e. ha$^{-1}$ = 506 g ha$^{-1}$ of surfactant = 0.26% (w/w) in 200 liters of spray solution

TABLE 7

The herbicidal activity (percent control) on *Stellaria media*, 21 days after treatment

| Herbicide dose (g a.e. ha$^{-1}$) | 750 | ±S.E. | 1500 | ±S.E. |
|---|---|---|---|---|
| Formulation 1 | 61.7 | 4.4 | 91.7 | 4.4 |
| Formulation B (comparison) | 58.3 | 1.7 | 81.7 | 4.4 |

*S.E. = standard error
750 g a.e. ha$^{-1}$ = 253 g ha$^{-1}$ of surfactant = 0.13% (w/w) in 200 liters of spray solution
1500 g a.e. ha$^{-1}$ = 506 g ha$^{-1}$ of surfactant = 0.26% (w/w) in 200 liters of spray solution

TABLE 8

The herbicidal activity (percent control) on *Stellaria media*, 30 days after treatment

| Herbicide dose (g a.e. ha$^{-1}$) | 750 | ±S.E. | 1500 | ±S.E. |
|---|---|---|---|---|
| Formulation 1 | 75.0 | 12.6 | 100.0 | 0.0 |
| Formulation B (comparison) | 66.7 | 3.3 | 93.3 | 6.7 |

*S.E. = standard error
750 g a.e. ha$^{-1}$ = 253 g ha$^{-1}$ of surfactant = 0.13% (w/w) in 200 liters of spray solution
1500 g a.e. ha$^{-1}$ = 506 g ha$^{-1}$ of surfactant = 0.26% (w/w) in 200 liters of spray solution In the overall comparison of the formulations for the different doses it was found that the formulations of the invention perform better than the prior art formulation B.

The invention claimed is:

1. An aqueous herbicidal composition comprising at least one phenoxy acid herbicide or an agriculturally acceptable salt or derivative thereof, and a surfactant adjuvant, wherein said surfactant adjuvant comprises at least one alkylamidopropyl dialkylamine surfactant having the formula $$R-N(H)-(CH_2)_n-N(Y)(Y') \quad (I)$$

wherein R is -a straight or branched chain, saturated or unsaturated acyl group having 6-22 carbon atoms, n is 3, and Y and Y' are, independently, an alkyl group having 1-4 carbon atoms or $(AO)_sH$, wherein AO is an alkyleneoxy group having 2-4 carbon atoms, and s is on average 1-10; provided that at least one of the groups Y and Y' is an alkyl group having 1-4 carbon atoms; or a salt thereof; wherein the quaternised derivatives of the alkylamidopropyldialkylamine surfactants are excluded.

2. The composition of claim 1 wherein R is a straight or branched chain, saturated or unsaturated acyl group having from 6 to 18 carbon atoms; at least one of Y and Y' is a C1-C4 alkyl group, and n is 3.

3. The composition of claim 2 wherein R is a straight or branched chain, saturated or unsaturated acyl group having from 6 to 14 carbon atoms; Y and Y' are methyl, and n is 3.

4. The composition of claim 2 wherein R is a straight or branched chain, saturated or unsaturated acyl group having from 6 to 10 carbon atoms.

5. The composition of claim 1 wherein said R is derived from a natural fatty acid.

6. The composition of claim 1 wherein said R group is derived from coco.

7. The composition of claim 1 wherein said R group is an acyl group having 8 to 10 carbon atoms.

8. The composition of claim 1 wherein said alkylamidopropyl dialkylamine surfactant is selected from the group consisting of N-[3-(dimethylamino)propyl] ($C_8$-$C_{10}$) amide, N-[3-(dimethylamino)propyl] cocoamide, and N-[3-(dimethylamino)propyl] (rape-seed) amide.

9. A herbicidal composition according to claims 1 wherein the phenoxy acid herbicide is a phenoxyacetic acid herbicide, phenoxybutyric acid herbicide, phenoxypropionic acid herbicide, aryloxyphenoxypropionic acid herbicide, or a mixture thereof.

10. A herbicidal composition according to claims 1 wherein the phenoxy acid herbicide is selected from the group consisting of 4-CPA, 2,4-D, 3,4-DA, MCPA, MCPA-thioethyl, 4-CPB, 2,4-DB, 3,4-DB, MCPB, cloprop, 4-CPP, dichlorprop dichlorprop-P, 3,4-DP, fenoprop, mecoprop, mecoprop-P, chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, trifop, 2,4,5-T, 2,4,5-TB, and mixtures thereof.

11. The composition of claim 10 wherein said phenoxy acid herbicide is a water-soluble 2,4 D salt.

12. The composition of claim 11 wherein the concentration of phenoxy acid is in the range of 100-800 g ae/l, and the ratio of phenoxy acid (wt % ae) to the surfactant adjuvant of formula I is between 1:2 and 25:1.

13. The composition of claim 12 wherein the concentration of phenoxy acid is in the range of 400-700 g ae/l, and the ratio of phenoxy acid (wt % ae) to the surfactant adjuvant of formula I is between 2.5:1 and 20:1.

14. The composition of claim 13 wherein the ratio of phenoxy acid (wt % ae) to the surfactant adjuvant of formula I is between 3:1 and 15:1.

15. The composition of claim 1 further comprising at least one co-herbicide.

16. The composition of claim 1 wherein said composition does not contain any water-insoluble solvent or water insoluble oil.

17. The composition of claim 1 further comprising an alkaline compound other than the compound of formula (I).

18. The composition of claim 17 where the alkaline compound is selected from the group consisting of dimethylamine, isopropylamine, triethylamine and diethanolamine.

19. The composition of claim 1 wherein said composition is an aqueous concentrate, wherein said aqueous concentrate contains phenoxy acid equivalent in the range of from 20 to 40%, and from about 2 to about 20% alkylamidopropyl dialkylamine surfactant.

20. A method of controlling unwanted vegetation, said method comprising applying to said unwanted vegetation an effective amount of a herbicidal composition according to claim 1.

21. The method of claim 20 wherein said herbicidal composition comprises the phenoxy acid herbicide 2, 4 D.

22. A method of making an aqueous herbicidal composition comprising mixing at least one phenoxy acid herbicide or an agriculturally acceptable salt or derivative thereof with a surfactant adjuvant, wherein the surfactant adjuvant comprises at least one alkylamidopropyl dialkylamine surfactant having the formula
wherein R is a straight or branched chain, saturated or unsaturated acyl group having 6-22

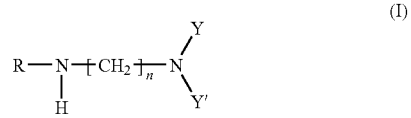

(I)

carbon atoms, n is 3, and Y and Y' are, independently, an alkyl group having 1-4 carbon atoms or $(AO)_sH$, wherein AO is an alkyleneoxy group having 2-4 carbon atoms, and s is on average 1-10; provided that at least one of the groups Y and Y' is an alkyl group having 1-4 carbon atoms; or a salt thereof; wherein the quaternised derivatives of the alkylamidopropyldialkylamine surfactants are excluded.

* * * * *